United States Patent [19]

Felman et al.

[11] Patent Number: 5,001,126

[45] Date of Patent: Mar. 19, 1991

[54] ANTI-ULCER 5-(2-SUBSTITUTED ETHENYL)-3(2H)-FURANONES

[75] Inventors: Steven W. Felman, Langhorne, Pa.; Ivo L. Jirkovsky, Plainsboro; Kevin A. Memoli, Cranbury, both of N.J.

[73] Assignee: American Home Products Corporation, New York, N.Y.

[21] Appl. No.: 571,962

[22] Filed: Aug. 23, 1990

Related U.S. Application Data

[62] Division of Ser. No. 449,620, Dec. 12, 1989, Pat. No. 4,966,905.

[51] Int. Cl.$^5$ .................. A61K 31/495; C07D 405/06
[52] U.S. Cl. ..................................... 514/255; 544/405
[58] Field of Search ........................ 544/405; 514/255

[56]         References Cited
         U.S. PATENT DOCUMENTS 4,931,459  6/1990  Baumgarth .......................... 544/405

OTHER PUBLICATIONS

Tsuge et al., Chem. Letters, 323, (1987).

Takashi et al., Chem. Abstracts, vol. 108, No. 13; 112103r, (1988).

Tsuge et al., Chem. Abstracts, vol. 107, No. 19, 175802t, (1987).

Ito et al., Chem. Abstracts, vol. 96, No. 17, 142535j, (1982).

Primary Examiner—Mary C. Lee
Assistant Examiner—J. Richter
Attorney, Agent, or Firm—Richard K. Jackson

[57]                ABSTRACT

A compound of the formula:

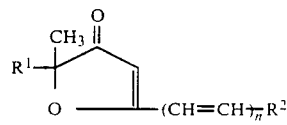

in which R is alkyl, phenyl or halophenyl; $R^2$ is substituted phenyl having from 1 to 3 substituents selected from halo, alkyl, alkylthio, alkylsulfonyl, cyano, trifluoromethyl, or $R^2$ is pyridinyl, pyrazinyl, quinolinyl, N-alkylpyrrolyl, thienyl, benzothienyl, or furyl; and n is 1 or 2, are cytoprotective anti-ulcer agents.

7 Claims, No Drawings

ANTI-ULCER 5-(2-SUBSTITUTED ETHENYL)-3(2H)-FURANONES

This is a division of application Ser. No. 07/449,620, now U.S. Pat. No. 4,966,905, filed Dec. 12, 1989.

DESCRIPTION OF THE INVENTION

In accordance with this invention, there is provided a group of novel 5-ethenyl-3(2H)-furanone derivatives, pharmaceutical compositions containing those novel compounds and a process for treating and/or preventing ulcers by administering certain 5-ethenyl-3(2H)-furanone derivatives to mammals in need of such cytoprotective-antiulcer treatment.

The novel compounds of this invention present the following structural formula:

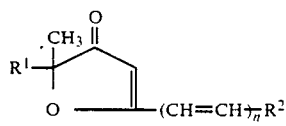

in which $R^1$ is alkyl of 1 to 6 carbon atoms, phenyl or halophenyl;

$R^2$ is substituted phenyl having from 1 to 3 substituents selected from halo, alkyl of 1 to 6 carbon atoms, alkylthio of 1 to 6 carbon atoms, alkylsulfonyl of 1 to 6 carbon atoms, cyano, trifluoromethyl, or $R^2$ is pyridinyl, pyrazinyl, quinolinyl, N-alkylpyrrolyl in which the alkyl substituent has 1 to 6 carbon atoms, thienyl, benzothienyl, or furyl; and n is 1 or 2.

Within that group of compounds, there resides a preferred subgenus of compounds based upon their profile of activity. This subgroup of compounds are of the formula:

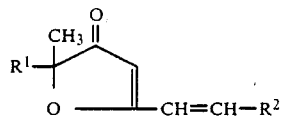

in which $R^1$ is methyl, phenyl or 4-fluorophenyl; and $R^2$ is bromo-, chloro-, fluoro-, dichloro, difluoro or cyano-substituted phenyl or $R^2$ is thienyl, pyridinyl, pyrazinyl or quinolinyl.

The pharmaceutical composition and method of use aspects of this invention involve both the novel compounds of the genus disclosed, supra, as well as the known compound 2,2-dimethyl-5-(2-phenylethenyl)-3(2H)-furanone (Chem. Lett., pp. 323–326, 1987, Chem. Soc. J.). The pharmaceutical compositions are best described as:

A compound of the formula:

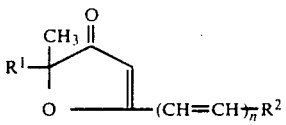

in which $R^1$ is alkyl of 1 to 6 carbon atoms, phenyl or halophenyl;

$R^2$ is phenyl or substituted phenyl having from 1 to 3 substituents selected from halo, alkyl of 1 to 6 carbon atoms, alkylthio of 1 to 6 carbon atoms, alkylsulfonyl of 1 to 6 carbon atoms, cyano, trifluoromethyl, or $R^2$ is pyridinyl, pyrazinyl, quinolinyl, N-alkylpyrrolyl in which the alkyl substituent has 1 to 6 carbon atoms, thienyl, benzothienyl, or furyl; and n is 1 or 2;

and a pharmaceutically acceptable carrier therefor.

The preferred pharmaceutical compositions involve the preferred compounds in conjunction with a pharmaceutically acceptable carrier.

The novel compounds of this invention are prepared by reaction of the appropriately substituted 2,5-dimethyl-3(2H)-furanone with an appropriately substituted aldehyde, thusly:

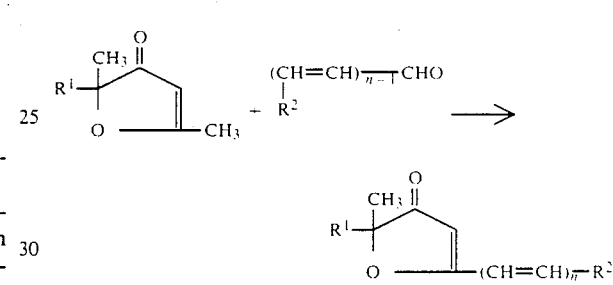

The products are produced in the trans (E)-isomeric form about the vinylene group(s).

The intermediate furanone derivatives are obtained by the following techniques.

The 2,2,5-trimethyl-3(2H)-furanone starting material is a known compound [J.A.C.S. 103 1501 (1981)]. It is readily prepared by hydrogenation of 3-methyl-5-(1-hydroxy-1-methylethyl)isoxazole, which in turn is obtainable by the addition of nitroethane to 2-methyl-3-butyn-2-ol in the presence of phosphorus oxychloride. The following detailed procedure illustrates the method used.

To a solution of 2-methyl-3-butyn-2-ol (675 mL, 6.97M), triethylamine (1500 mL, 10.76M), and nitroethane (350 mL, 4.0M) in chloroform (4 L) at 10° C. was added a solution of phosphorus oxychloride (438 mL, 4.72M) in chloroform (1.5 L) dropwise over eight hours. After the addition, the reaction solution was warmed to room temperature and was stirred overnight. The reaction solution was then washed with water (2×2 L), saturated aqueous sodium bicarbonate (2×2 L), dried over sodium sulfate and filtered. After the solvent was removed under reduced pressure, the dark residual oil was distilled (85° C., 1 mm) to give a dark orange liquid (343 g, 49.7%) $^1$H NMR (CDCl$_3$, 100 MHz): δ 6.05 (s, 1H), 3.08 (brs, 1H), 2.16 (s, 3H), 1.54 (s, 6H).

To a solution of 10% palladium on charcoal (50 g) in MeOH (800 mL) under nitrogen was added a solution of 3-methyl-5-(1-hydroxy-1-methylethyl)-isoxazole (109 g, 0.77M) in MeOH (200 mL). The reaction mixture was hydrogenated at 30 psi in a Parr hydrogenation apparatus till there was no more hydrogen uptake. The catalyst was removed by filtration under nitrogen and washed with MeOH (2×100 mL). The resulting filtrate was concentrated under reduced pressure to yield a white crystalline solid (106.2 g).

This product was suspended in water (200 mL) and 1N hydrochloric acid (400 mL) and stirred for 2 hours. The reaction mixture was then neutralized with solid sodium bicarbonate and saturated with sodium chloride. The aqueous solution was extracted with diethyl ether (5×100 mL). The combined ethereal extracts were dried over magnesium sulfate, filtered and concentrated under reduced pressure to give a yellow liquid (82.7 g, 85% from the isoxazole). This procedure was repeated and the combined crude products were distilled (bp=100°-102° C. at 1 mm) to yield 2,2,5-trimethyl-3(2H)-furanone as a clear liquid (140 g, 72%). $^1$H NMR (CDCl$_3$, 100 MHz): δ 5.36 (s, 1H), 2.21 (s, 3H), 1.40 (s, 6H).

The 2,5-dimethyl-2-phenyl-3(2H)-furanone reactant is prepared as follows:

To a solution of acetaldoxime (44.5 g, 0.75M), 3-butyn-2-ol (52.9 g, 0.75M) and triethylamine (10.5 mL, 0.075M), in dichloromethane (1.75 L) at 0° C., was added a 5% aqueous solution of sodium hypochlorite (bleach, 1.94 kg) over three hours. The reaction mixture was warmed to room temperature and allowed to stir overnight.

The layers were separated and the aqueous layer was extracted with dichloromethane 5×100 mL). The combined dichloromethane extracts were washed with saturated aqueous sodium chloride (500 mL), dried over MgSO$_4$, filtered and concentrated under reduced pressure to give 3-methyl-5-(1-hydroxyethyl)-isoxazole as a yellow oil (47.7 g, 50%) that was used without further purification. $^1$H NMR (CDCl$_3$, 100 MHz): δ 6.25 (s, 1H), 4.95 (q, J=5 Hz, 1H), 2.25 (s, 3H), 1.53 (d, J=5 Hz, 3H).

To a solution of 3-methyl-5-(1-hydroxyethyl)-isoxazole (47.6 g, 367 mM) in acetone (2 L) at 0° C., was added a solution of chromic anhydride (93.3 g, 933 mM), 6N aqueous sulfuric acid (186.15 mL, 1.1M) and water (186 mL) over two hours. After the reaction solution was allowed to warm to room temperature, saturated aqueous sodium chloride was added. The aqueous layer was extracted with dichloromethane (3×400 mL). The combined organic extracts were washed with saturated aqueous sodium sulfite (2×300 mL) and saturated aqueous sodium chloride (2×300 mL). The organic layer was dried over MgSO$_4$, filtered and concentrated under reduced pressure to give 3-methyl-5-acetoxy-isoxazole as a yellow powder (27.8 g, 60%) that was used without further purification. $^1$H NMR (CDCl$_3$, 100 MHz): δ 7.55 (s, 1H), 2.65 (s, 3H), 2.43 (s, 3H).

To a solution of 3-methyl-5-acetoxy-isoxazole (14 g, 112 mM) in diethyl ether (400 mL) at 0° C., was added a 3M solution of phenylmagnesium bromide in diethyl ether (44.7 mL, 134 mM) dropwise. After the addition was complete, the reaction mixture was stirred for 30 minutes. When pH 7 buffer (100 mL) was added, the layers were separated. The aqueous layer was extracted with diethyl ether (2×75 mL). The combined ethereal extracts were washed with saturated aqueous sodium chloride (50 mL), dried over MgSO$_4$, filtered and concentrated under reduced pressure to give 3-methyl-5-(1-hydroxy-1-phenylethyl)-isoxazole as an amber oil (20.2 g, 89%) that was used without further purification. $^1$H NMR (CDCl$_3$, 100 MHz): δ 7.40 (m, 5H), 6.0 (s, 1H), 2.38 (s, 3H), 1.87 (s, 3H).

The catalyst (10% Pd/C, 20 g) was suspended in methanol (800 mL) and a solution of 3-methyl-5-(1-hydroxy-1-phenylethyl)-isoxazole (20.2 g, 99.4 mM) in methanol (200 mL) was added. The reaction mixture was hydrogenated under 20 psi until there was no more uptake of hydrogen. After the reaction mixture was degassed, the catalyst was removed by filtration and the filtrate was concentrated under reduced pressure.

The above crude product was dissolved in 1N aqueous hydrochloric acid (100 mL) and methanol (100 mL) and stirred one hour. Then the reaction solution was neutralized with solid sodium bicarbonate and diluted with saturated aqueous sodium chloride (200 mL). The aqueous solution was extracted with diethyl ether (4×100 mL). The combined ethereal extracts were dried over MgSO$_4$, and concentrated under reduced pressure to afford 2,5-dimethyl-2-phenyl-3(2H)-furanone as a yellow oil (12.5 g, 67%) that was used without further purification. $^1$H NMR (CDCl$_3$, 100 MHz): δ 7.42 (m, 5H), 5.42 (s, 1H), 2.32 (s, 3H), 1.73 (s, 3H).

The intermediate 2,5-dimethyl-2-(4-fluorophenyl)-3(2H)-furanone is produced in the same manner as the 2-phenyl analogue, supra. Thus, to a solution of 3-methyl-5-acetoxy-isoxazole (0.5 g, 4 mM) in diethyl ether (25 mL) at 0° C., was added a 2N ethereal solution of phenylmagnesium bromide in diethyl ether (2.4 mL, 4.8 mM), dropwise. After the addition was complete, the reaction mixture was stirred 30 minutes. When pH 7 buffer (10 mL) was added, the layers were separated. The aqueous layer was extracted with diethyl ether (2×25 mL). The combined ethereal extracts were washed with saturated aqueous sodium chloride (10 mL), dried over MgSO$_4$, filtered and concentrated under reduced pressure to give 3-methyl-5-[1-hydroxyl-1-(4-fluorophenyl)ethyl]-isoxazole as an amber oil (0.8 g, 91%) that was used without further purification. $^1$H NMR (CDCl$_3$, 100 MHz): δ 7.4 (dd, J$_1$=6 Hz, J$_2$=2.5 Hz, 2H), 7.0 (t, J=5 Hz, 2H), 5.95 (s, 3H), 2.25 (s, 3H), 1.88 (s,3H).

The catalyst (10% Pd/C, 15 g) was suspended in methanol (400 mL), and a solution of 3-methyl-5-[1-hydroxy-1-(4-fluorophenyl)ethyl]isoxazole (15 g, 73.8 mM) in methanol (100 mL) was added. The reaction mixture was hydrogenated under 20 psi until there was no more uptake of hydrogen. After the reaction mixture was degassed, the catalyst was filtered and the filtrate was concentrated under reduced pressure.

The above crude product was dissolved in 1N aqueous hydrochloric acid (100 mL) and methanol (100 mL) and stirred for one hour. Then the reaction solution was neutralized with solid sodium bicarbonate and diluted with saturated aqueous sodium chloride (100 mL). The aqueous solution was extracted with diethyl ether (4×100 mL). The combined ethereal extracts were dried over MgSO$_4$, filtered and concentrated under reduced pressure to afford 2-methyl-2-(4-fluorophenyl)-5-methyl-3(2H)-furanone as a yellow oil (10.7 g, 67%) that was used without further purification. $^1$H NMR (CDCl$_3$, 100 MHz): δ 7.49 (dd, J$_1$=6 Hz, J$_2$=2.5 Hz, 2H), 7.02 (t, J=8 Hz), 5.42 (s, 1H), 2.35 (s, 3H), 1.72 (s, 3H).

The following examples illustrate the preparation of the novel compounds of this invention. In each instance, the trans-isomer of the named product was obtained.

EXAMPLE 1

2,2-Dimethyl-5-[2-(3,4,5-trimethoxyphenyl)ethenyl]-3(2H)-furanone

To a mixture of 2,2,5-trimethyl-3(2H)-furanone (2.5 g, 19.8 mM) and 3,4,5-trimethoxybenzaldehyde (4.7 g, 23.8 mM) in ethanol was added 1N aqueous sodium hydroxide (4 mL, 4mM). After the reaction mixture was stirred for 48 hours at room temperature, the solution was concentrated to 50 mL and diluted with water (300 mL). The aqueous layer was extracted with diethyl ether (4×100 mL). The combined ethereal extracts were washed with saturated aqueous sodium chloride (50 mL), dried over magnesium sulfate, filtered and concentrated under reduced pressure to afford a dark yellow crystalline solid. The crude product was purified by chromatography (silica gel, petroleum ether-ethyl acetate) to give light yellow crystals (5.0 g, 83% yield), m.p. 149°–150° C.

Elemental analysis for $C_{17}H_{20}O_5$: Calc'd: C, 67.09; H, 6.62. Found: C, 66.98; H, 6.67.

81% inhibition at 25 mg/kg.

EXAMPLE 2

2,2-Dimethyl-5-[2-(4-fluorophenyl)ethenyl]-3(2H)-furanone

To a solution of 2,2,5-trimethyl-3(2H)-furanone (2.0 g, 15.9 mM) and 4-fluorobenzaldehyde (1.6 g, 13.2 mM) in ethanol (100 mL), was added 1N aqueous sodium hydroxide (1.6 mL, 1.6 mM). The reaction solution was heated at 50° C. for four hours. After the reaction solution was cooled to room temperature and diluted with saturated aqueous sodium chloride (200 mL) and water (200 mL), the aqueous solution was extracted with diethyl ether (2×100 mL). The combined ethereal extracts were washed with saturated aqueous sodium chloride (25 mL), dried over magnesium sulfate, filtered and concentrated at reduced pressure to afford a dark yellow crystalline solid. The crude product was recrystallized from hexane to give light yellow crystals (1.8 g, 45% yield), m.p. 55°–57° C.

Elemental analysis for $C_{14}H_{13}O_2F$: Calc'd: C, 72.40; H, 5.64. Found: C, 72.05; H, 5.74.

$ED_{50}$ 11 mg/kg.

EXAMPLE 3

5-[2-(2,4-Difluorophenyl)ethenyl]-2,2-dimethyl-3(2H)-furanone

To a solution of dry diisopropylamine (3.3 mL, 24 mM) in dry tetrahydrofuran (25 mL) at −78° C., was added dropwise 2.3N solution of n-butyllithium in hexane (10.4 mL, 24mM). After the reaction solution was stirred 15 minutes, a solution of 2,2,5-trimethyl-3(2H)-furanone (2.0 g, 16 mm) in tetrahydrofuran (10 mL) was added dropwise. Hexamethylphosphoramide (4.4 mL, 24 mM) was then added dropwise after 30 minutes. Finally, 2,4-difluorobenzaldehyde (3.5 mL, 31.8 mM) in tetrahydrofuran (10 mL) was added in one portion. The reaction solution was stirred 10 minutes when trifluoroacetic anhydride (11.87 g, 55.7 mM) was added in one portion. Again, the reaction solution was stirred 15, minutes when triethylamine (5.6 g, 55.7 mM) was added and was allowed to warm to room temperature. The reaction solution was partitioned between saturated aqueous sodium chloride (50 mL) and diethyl ether (50 mL). The layers were separated. The organic layers were then washed with saturated aqueous sodium chloride (2×25 mL), dried over MgSO4, filtered and concentrated under reduced pressure to give an orange liquid. The crude product was purified by chromatography (silica gel, pet. ether-ethyl acetate) to afford a yellow crystalline solid (2.6 g, 65% yield), m.p. 98.5°–100° C.

Elemental analysis for $C_{14}H_{12}F_2O_2$: Calc'd: C, 67.20; H, 4.83. Found: C, 66.99; H, 5.12.

52% inhibition at 25 mg/kg.

EXAMPLE 4

5-[2-(3,4-Difluorophenyl)ethenyl]-2,2-dimethyl-3(2H)-furanone

To a solution of 3,4-difluorobenzaldehyde (1.9 g, 13.2 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was heated at 50° C. for four hours. After the reaction solution was cooled to room temperature, saturated aqueous sodium chloride (400 mL) was added. The aqueous layer was extracted with diethyl ether (3×100 mL). The combined ethereal extracts were washed with saturated aqueous sodium chloride (50 mL), dried over MgSO4, filtered and concentrated to give a yellow solid. The crude product was triturated with 10% diethyl ether/pet. ether (50 mL) to give a pale yellow solid (1.66 g, 50% yield), m.p. 105°–106° C.

Elemental analysis for $C_{14}H_{12}F_2O_2$: Calc'd: C, 67.20; H, 4.83. Found: C, 67.08; H, 4.80.

47% inhibition at 25 mg/kg.

EXAMPLE 5

(E)-2,2-Dimethyl-5-[2-(4-bromophenyl)ethenyl]-3(2H)-furanone

To a solution of dry diisopropylamine (3.3 mL, 24 mM) in dry tetrahydrofuran (25 mL) at −78° C., was added dropwise a 2.3N solution of n-butyllithium in hexane (10.4 mL, 24 mM). After the reaction solution was stirred for 15 minutes, a solution of 2,2,5-trimethyl-3(2H)-furanone (2.0 g, 16 mM) in tetrahydrofuran (10 mL) was added dropwise. Hexamethylphosphoramide (4.4 mL, 24 mM) was then added dropwise for 30 minutes. Finally, p-bromobenzaldehyde (3.6 g, 19.2 mM) in tetrahydrofuran (10 mL) was added in one portion. The reaction solution was stirred 10 minutes when trifluoroacetic anhydride (5.6 mL, 40 mM) was added in one portion. Again, the reaction solution was stirred for 15 minutes when triethylamine (5.9 mL, 47.6 mM) was added and was allowed to room temperature. The reaction mixture was then partitioned between saturated aqueous sodium chloride (50 mL) and diethyl ether (50 mL). The layers were separated. The organic layers were then washed with saturated aqueous sodium chloride (2×25 mL), dried over MgSO4, filtered and concentrated under reduced pressure to give dark liquid. After the crude product was dissolved in dichloromethane (100 mL), trifluoroacetic anhydride (5.6 mL, 40 mM) was added. After thirty minutes, triethylamine (2.75 mL, 20 mM) was added. The resulting mixture was stirred for one hour, washed with 1N aqueous hydrochloric acid, dried over magnesium sulfate, filtered and concentrated under reduced pressure to afford an amber oil. The crude oil was purified by chromatography (silica gel, petroleum ether-ethyl acetate) to give yellow-brown crystals (1.8 g, 39%). Recrystallization from hexane gave an analytically pure product, m.p. 109°–110° C.

Elemental analysis for $C_{14}H_{13}BrO_2$: Calc'd: C, 57.36; H, 4.47. Found: C, 57.44; H, 4.50.

63% inhibition at 25 mg/kg.

EXAMPLE 6

2,2-Dimethyl-5-[2-(4-chlorophenyl)ethenyl]-3(2H)-furanone

To a solution of dry diisopropylamine (5.0 mL, 35.7 mM) in dry tetrahydrofuran (150 mL) at −78° C., was added dropwise a 2.3 N solution of nbutyllithium in hexane (15.5 mL, 35.7 mM). After the reaction solution was stirred 15 minutes, a solution of 2,2,5-trimethyl-3(2H)-furanone (3.0 g, 23.8 mM) in tetrahydrofuran (25 mL) was added dropwise. Hexamethylphosphoramide (6.4 mL, 34.7 mM) was added dropwise after 30 minutes. Finally, p-chlorobenzaldehyde (3.0 g, 2.7.8 mM) in tetrahydrofuran (25 mL) was added in one portion. The reaction solution was stirred 15 minutes when trifluoroacetic anhydride (10.5 mL, 276 mM) was added in one portion. Again the reaction mixture was stirred 15 minutes when triethylamine (5.9 mL, 48 mM) was added and the mixture was allowed to warm to room temperature. The reaction mixture was then partitioned between saturated aqueous sodium chloride (50 mL) and diethyl ether (50 mL). The organic layer was separated and washed with saturated aqueous sodium bicarbonate (2×25 mL) and saturated aqueous sodium chloride (25 mL). The organic layer was dried over magnesium sulfate, filtered and concentrated under reduced pressure to give an orange liquid which was purified by chromatography (silica gel, pet. ether-ethyl acetate) to afford yellow crystals (3.8 g, 65% yield), m.p. 91°–92° C.

Elemental analysis for $C_{14}H_{13}ClO_2$: Calc'd: C, 67.61; H, 5.27. Found: C, 67.67; H, 5.56.

$ED_{50}$ 10.3 mg/kg.

EXAMPLE 7

5-[4-(4-Chlorophenyl)-1,3-butadienyl]-2,2-dimethyl-3(2H)-furanone

To a solution of p-chlorocinnamaldehyde (2.7 g, 16.2 mM) and 2,2,5-trimethyl-3(2H)-furanone (2.45 g, 19.4 mM) in ethanol (100 mL), was added 1N aqueous sodium hydroxide (32 mL, 3.2 mM). The reaction solution was stirred at room temperature for one day. After saturated aqueous sodium chloride (400 mL) was added, the aqueous layer was extracted with diethyl ether (3×100 mL). The combined ethereal extracts were washed with saturated aqueous sodium chloride (50 mL), dried over MgSO$_4$, filtered and concentrated to give a brown solid. The crude product was purified by chromatography (silica gel, pet. ether-ethyl acetate) to afford yellow crystals (1.9 g, 36% yield), m.p. 95°–96° C.

Elemental analysis for $C_{16}H_{15}ClO_2$: Calc'd: C, 69.95; H, 5.50. Found: C, 69.99 H, 5.57.

EXAMPLE 8

5-[2-(2,4-Dichlorophenyl)ethenyl]-2,2-dimethyl-3(2H)-furanone

To a solution of 2,4-dichlorobenzaldehyde (2.3 g, 13.2 mM) and 2,2,5-trimethyl-3(2H)-furanone (2.0 g, 15.9 mM) in ethanol (100 mL) was added 1N aqueous sodium hydroxide (1.6 mL, 1.6 mM). The reaction solution was heated at 60° C. for 4 hours. After the reaction solution was cooled, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a yellow solid. The crude product was triturated with 10% diethyl ether/pet. ether to afford a light yellow powder (2.6 g, 70% yield), m.p. 154°–156° C.

Elemental analysis for $C_{14}H_{12}Cl_2O_2$: Calc'd: C, 59.39; H, 4.27. Found: C, 59.26; H, 4.17.

EXAMPLE 9

5-[2-(3,4-Dichlorophenyl)ethenyl]-2,2-dimethyl-3(2H)-furanone

To a solution of 3,4-dichlorobenzaldehyde (2.3 g, 13.2 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was heated at 60° C. for 4 hours. After the reaction solution cooled, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a yellow solid. The crude product was purified by chromatography (silica gel, pet. ether/ethyl acetate) to afford a light yellow solid (2.1 g, 56% yield), m.p. 100°–102° C.

Elemental analysis for $C_{14}H_{12}Cl_2O_2$: Calc'd: C, 59.39; H, 4.27. Found: C, 59.03; H, 4.14.

EXAMPLE 10

5-[2-(3,5-Dichlorophenyl)ethenyl]-2,2-dimethyl-3(2H)-furanone

To a solution of 3,5-dichlorobenzaldehyde (2.3 g, 13.2 mM) and 2,2,5-trimethyl-3(2H)-furanone (2.0 gm, 15.9 mM) in ethanol (100 mL), was added 1N aqueous sodium hydroxide (1.6 mL, 1.6 mM). The reaction solution was heated at 60° C. for 4 hours. After the reaction solution was cooled, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a yellow solid. The crude product was purified by chromatography (silica gel, pet. ether/ethyl acetate) to afford a light yellow solid (1.7 g, 45% yield), m.p. 129°–131° C.

Elemental analysis for $C_{14}H_{12}Cl_2O_2$: Calc'd: C, 59.39; H, 4.27. Found: C, 59.30; H, 3.9.

$ED_{50}$ 9 mg/kg.

EXAMPLE 11

2,2-Dimethyl-5-[2-[4-(trifluoromethyl)phenyl]ethenyl]-3(2H)-furanone

To a solution of dry diisopropylamine (5.0 mL, 35.7 mM) in dry tetrahydrofuran (150 mL) at −78° C., was added dropwise a 2.3N solution of n-butyllithium in hexane (15.5 mL, 35.7 MM). After the reaction solution was stirred 15 minutes, a solution of 2,2,5-trimethyl-3(2H)-furanone (3.0 g, 23.8 mM) in tetrahydrofuran (25 mL) was added dropwise. Hexamethylphosphoramide (6.4 mL, 35.7 mM) was then added dropwise after 30 minutes. Finally, p-trifluoromethylbenzaldehyde (4.0 g, 28.5 mM) in tetrahydrofuran (25 mL) was added in one portion. The reaction solution was stirred 15 minutes when trifluoroacetic anhydride (10.5 mL, 76 mM) was added. Again the reaction solution was stirred 15 minutes when triethylamine (5.9 mL, 48 mM) was added and the mixture was allowed to warm to room temperature. The reaction mixture was partitioned between diethyl ether (50 mL) and saturated aqueous sodium chloride (100 mL). The organic layer was separated and washed with saturated aqueous sodium bicarbonate (2×25 mL), and saturated aqueous sodium chloride (50 mL). The organic layer was dried over magnesium sulfate, filtered and concentrated under reduced pressure to give an amber liquid. The crude product was purified by chromatography (silica gel, petroleum ether-ethyl acetate) to give yellow crystals (3.2 g, 71% yield), m.p. 94°–95° C.

Elemental analysis for $C_{15}H_{13}F_3O_2$: Calc'd: C, 63.83; H, 4.64. Found: C, 63.83; H, 4.74.

30% inhibition at 25 mg/kg.

EXAMPLE 12

(E)-2,2-Dimethyl-5-[2-[4-(methylthio)phenyl]ethenyl]-3(2H)-furanone

To a solution of dry diisopropylamine (5.0 mL, 35.7 mM) in dry tetrahydrofuran (150 mL) at −78° C., was added dropwise a 2.3N solution of n-butyllithium in hexane (15.5 mL, 35.7 mM). After the reaction solution was stirred for 15 minutes, a solution of 2,2,5-trimethyl-3(2H)-furanone (30 g, 23.8 mM) in tetrahydrofuran (25 mL) was added dropwise. Hexamethylphosphoramide (6.4 mL, 34.7 mM) was then added dropwise after 30 minutes. Finally, p-methylthiobenzaldehyde (43 g, 28.5 mM) in tetrahydrofuran (25 mL) was added in one portion. The reaction solution was stirred 15 minutes when trifluoroacetic anhydride (10.5 mL, 75 mM) was added in one portion. Again, the reaction solution was stirred 15 minutes when triethylamine (5.9 mL, 48 mM) was added and was allowed to warm to room temperature. Then the reaction mixture was partitioned between saturated aqueous sodium chloride (50 mL) and diethyl ether (50 mL). The organic layer was separated and washed with saturated aqueous sodium bicarbonate (2×25 mL) and saturated aqueous sodium chloride (25 mL). The organic layer was dried over magnesium sulfate, filtered and concentrated under reduced pressure to give an amber liquid. The crude product was purified by chromatography (silica gel, pet. ether-ethyl acetate) to afford yellow crystals (3.0 g, 48% yield), m.p. 98°–99.5° C.

Elemental analysis for $C_{15}H_{16}O_2S$: Calc'd: C, 69.20; H, 6.19. Found: C, 68.91; H, 6.35.

5% inhibition at 25 mg/kg.

EXAMPLE 13

2,2-Dimethyl-5-[2-[4-(methylsulfonyl)phenyl]ethenyl]-3(2H)-furanone

A solution of 2,2,5-trimethyl-3(2H)-furanone (1.5 g, 11.9 mM), 4-methylthiobenzaldehyde (2.2 g, 14.3 mM) and 1N aqueous sodium hydroxide (1.2 mL, 1.2 mM) in ethanol (30 mL) was stirred 16 hours at room temperature. The reaction solution was diluted with saturated aqueous sodium chloride (200 mL) and was extracted with diethyl ether (3×100 mL). The combined ethereal extracts were washed with saturated aqueous sodium chloride (50 mL), dried over magnesium sulfate, filtered and concentrated under reduced pressure to give a yellow solid. The crude product was dissolved in dichloromethane (200 mL) then m-chloroperbenzoic acid (6.15 g, 35.63 mM) was added and the reaction mixture was stirred 4 hours at room temperature. Then the mixture was washed with 0.5M aqueous sodium sulfite (50 mL and saturated aqueous sodium bicarbonate (2×50 mL). The resulting solution was dried over $MgSO_4$, filtered and concentrated under reduced pressure to give a yellow solid. The crude product was purified by column chromatography (silica gel, pet. ether-ethyl acetate) to afford pale yellow crystals (1.76 g, 76% yield from ketone), m.p. 159°–160° C.

Elemental analysis for $C_{15}H_{16}O_4S$: Calc'd: C, 61.62; H, 5.52. Found: C, 61.44; H, 5.48.

56% inhibition at 25 mg/kg.

$ED_{50}$ 10.6 mg/kg.

EXAMPLE 14

4-[2-(2,3-Dihydro-2,2-dimethyl-3-oxo-5-furanyl)ethenyl]benzonitrile

A solution of 2,2,5-trimethyl-3(2H)-furanone (1.5 g, 11.9 mM), 4-cyanobenzaldehyde (1.7 g, 13.1 mM) and 1N aqueous sodium hydroxide (1.2 mL, 1.2 mM) in ethanol (50 mL) was stirred 24 hours at room temperature. The reaction mixture was diluted with saturated aqueous sodium chloride (200 mL) and extracted with diethyl ether (3×100 mL). The combined ethereal extracts were washed with saturated aqueous sodium chloride (50 mL), dried over $MgSO_4$, filtered and concentrated under reduced pressure to give a yellow solid. The crude product was purified by column chromatography (silica gel, 9:1, hexane-ethyl acetate) to afford pale yellow crystals (1.5 g, 53% yield), m.p. 169.5°–170.5° C.

Elemental analysis for $C_{15}H_{13}NO_2$: Calc'd: C, 75.30; H, 5.48; N, 4.85. Found: C, 75.23; H, 5.85; N, 5.86.

$ED_{50}$ 15 mg/kg.

EXAMPLE 15

3-[2-(2,3-Dihydro-2,2-dimethyl-3-oxo-5-furanyl)ethenyl]benzonitrile

A solution of 3-cyanobenzaldehyde (2.5 g, 19 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was stirred for one day at room temperature. After saturated aqueous sodium chloride (400 mL) was added, the aqueous layer was extracted with diethyl ether (3×100 mL). The combined ethereal extracts were washed with saturated aqueous sodium chloride (50 mL), dried over $MgSO_4$, filtered and concentrated to give a yellow solid. The product was recrystallized from hexane-ethyl acetate to afford an analytically pure sample (1.5 g, 43% yield), m.p. 155°–157° C.

Elemental analysis for $C_{15}H_{13}NO_2$: Calc'd: C, 75.30; H, 5.48; N, 5.85. Found: C, 75.09; H, 5.25; N, 5.92.

EXAMPLE 16

2,2-Dimethyl-5-[2-(1-methyl-2-pyrrolyl)ethenyl]-3(2H)-furanone

To a solution of 1-methyl-2-pyrrolecarboxaldehyde (1.4 g, 12.7 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was heated at 70° C. for 48 hours. After the reaction solution was cooled to 0° C., saturated aqueous sodium chloride (400 mL) was added. The aqueous layer was extracted with ethyl acetate (3×100 mL). The combined ethyl acetate extracts were washed with saturated aqueous sodium chloride (50 mL), dried over MgSO$_4$, filtered and concentrated to give a brown solid. The crude product was purified by chromatography (silica gel, pet. ether-ethyl acetate) to give orange crystals (1.8 g, 65% yield), m.p. 98.5°–100° C.

Elemental analysis for C$_{13}$H$_{15}$NO$_2$: Calc'd: C, 71.87; H, 6.96; N, 6.45. Found: C, 71.83; H, 7.00; N, 6.37.

32% inhibition at 10mg/kg.

EXAMPLE 17

2,2-Dimethyl-5-[2-(2-pyridinyl)ethenyl]-3(2H)-furanone

To a solution of 2-pyridinecarboxaldehyde (1.1 g, 9.9 mM) and 2,2,5-trimethyl-3(2H)-furanone (1.5 g, 11.9 mM) in ethanol (100 mL), was added 1N aqueous sodium hydroxide (1.2 mL, 1.2 mM). The reaction solution was stirred at room temperature for 2 days. After saturated aqueous sodium chloride (400 mL) was added, the aqueous layer was extracted with diethyl ether (3×100 mL). The combined ethereal extracts were washed with saturated aqueous sodium chloride (50 mL), dried over MgSO$_4$, filtered and concentrated to give a brown solid. The residue was purified by chromatography (silica gel, pet. ether/ethyl acetate) to yield yellow crystals (1.6 g, 75% yield), m.p. 87.5°–89.0° C.

Elemental analysis for C$_{13}$H$_{13}$NO$_2$: Calc'd: C, 72.56; H, 6.09; N, 6.51. Found: C, 72.62; H, 6.36; N, 6.59.

ED$_{50}$ 9 mg/kg.

EXAMPLE 18

2,2-Dimethyl-5-[2-(4-pyridinyl)ethenyl]-3(2H)-furanone

To a solution of dry diisopropylamine (2.6 mL, 19.1 mM) in dry tetrahydrofuran (350 mL) at −78° C., was added dropwise a 2.5M solution of n-butyllithium in hexane (7.6 mL, 19.1 mM). After the reaction solution was stirred for 15 minutes, a solution of 2,2,5-trimethyl-3(2H)-furanone (20 g, 15.9 mM) in tetrahydrofuran (25 mL) was added dropwise. Hexamethylphosphoramide (6.4 mL, 35.7 mM) was then added after 30 minutes. Finally, 4-pyridinecarboxaldehyde (2.5 g, 23.5 mM) in tetrahydrofuran (25 mL) was added in one portion. The reaction solution was stirred 15 minutes when trifluoroacetic anhydride (6.7 mL, 47.7 mM) was added in one portion. Again, the reaction solution was stirred 15 minutes before triethylamine (11 mL, 80 mM) was added and was allowed to warm to room temperature. The reaction mixture was concentrated to 100 mL then diluted with diethyl ether (300 mL). The organic layer was extracted with 1N aqueous hydrochloric acid (100 mL). The acid layer was neutralized with solid sodium bicarbonate and washed with diethyl ether (2×100 mL). The combined etheral layers were washed with saturated aqueous sodium chloride (2×50 mL), dried over MgSO$_4$, filtered and concentrated under reduced pressure to give a brown crystalline solid. The crude product was purified by chromatography (silica gel, pet. ether/ethyl acetate) to afford a yellow crystalline solid (935 mg, 32% yield), m.p. 94°–96° C.

Elemental analysis for C$_{13}$H$_{13}$NO$_2$: Calc'd: C, 72.54; H, 6.09; N, 6.51. Found: C, 72.21; H, 6.43; N, 6.89.

ED$_{50}$ 4 mg/kg.

EXAMPLE 19

2,2-Dimethyl-5-[2-(3-pyridinyl)ethenyl]-3(2H)-furanone

To a solution of 3-pyridinecarboxaldehyde (1.4 g, 13.2 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was stirred at room temperature for one day. After saturated aqueous sodium chloride (400 mL) was added, the aqueous layer was extracted with diethyl ether (3×100 mL). The combined ethereal extracts were washed with saturated aqueous sodium chloride (50 mL), dried over MgSO$_4$, filtered and concentrated to give a yellow solid. The crude product was purified by chromatography (silica gel, hexane/ethyl acetate) to afford a white crystalline solid (1.5 g, 53% yield), m.p. 68°–70° C.

Elemental analysis for C$_{13}$H$_{13}$NO$_2$: Calc'd: C, 72.54; H, 6.09; N, 6.51. Found: C, 72.73; H, 6.04; N, 6.50.

ED$_{50}$ 9.3 mg/kg.

EXAMPLE 20

5-[2-(4-Quinolinyl)ethenyl]-2,2-dimethyl-3(2H)-furanone

To a solution of 4-quinolinecarboxaldehyde (2.8 g, 17.8 mM) and 2,2,5-trimethyl-3(2H)-furanone (1.5 g, 11.9 mM) in ethanol (100 mL), was added 1N aqueous sodium hydroxide (1.2 mL, 1.2 mM). After the reaction solution was stirred for 4 hours, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a brown oil. The crude product was purified by column chromatography (silica gel, pet. ether-ethyl acetate) to yield a yellow crystalline solid (1.2 g, 32% yield), m.p. 117°–118° C.

Elemental analysis for C$_{17}$H$_{15}$NO$_2$: Calc'd: C, 76.96; H, 5.70; N, 5.28. Found: C, 76.99; H, 5.49; N, 5.25.

ED$_{50}$ 2.5 mg/kg.

EXAMPLE 21

2,2-Dimethyl-5-[2-(2-pyrazinyl)ethenyl]-3(2H)-furanone

To a solution of 2,2,5-trimethyl-3(2H)-furanone (2.1 g, 16.7 mM) and pyrazine carboxaldehyde (1.8 g, 16.7 mM) in ethanol (75 mL) was added 1,8-diazbicyclo[5.4.0]undec-7-ene (DBU, 0.26 g, 1.7 mM). The resulting solution was stirred overnight. Then the reaction solution was heated at 60° C. for 4 hours. After the reaction solution was cooled to room temperature, it was diluted with saturated aqueous sodium chloride (200 mL). The aqueous layer was extracted with dichloromethane (3×100 mL). The combined organic extracts were dried over sodium sulfate, filtered and concentrated under reduced pressure to afford a dark solid. Purification by column chromatography (silica gel, hexane-ethyl acetate) gave a pale yellow solid (1.6 g, 44% yield). Analytically pure product was obtained by recrystallization from hexane, m.p. 120.5°–121.5° C.

Elemental analysis for C$_{12}$H$_{12}$N$_2$O$_2$: Calc'd: C, 66.65; H, 5.59; N, 12.95. Found: C, 66.69; H, 5.68; N, 12.81.

56% inhibition at 10 mg/kg.

EXAMPLE 22

2,2-Dimethyl-5-[2-(3-thienyl)ethenyl]-3(2H)-furanone

To a solution of 3-thiophenecarboxaldehyde (1.5 g, 13.2 mM) and 2,2,5-trimethyl-3(2H)-furanone (1.5 g, 12 mM) in ethanol (100 mL), was added 1N aqueous sodium hydroxide (1.2 mL, 1.2 mM), the reaction solution heated to 60° C. for 4 hours. After the reaction solution cooled, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a yellow crystalline solid. The residue was purified by chromatography (silica gel, hexane/ethyl acetate) to yield yellow crystals (2.1 g, 72% yield), m.p. 79°–80° C.

Elemental analysis for $C_{12}H_{12}O_2S$; Calc'd: C, 65.43; H, 5.49. Found: C, 65.18; H, 5.62.

ED$_{50}$4 mg/kg.

EXAMPLE 23

2,2-Dimethyl-5-[2-(2-thienyl)ethenyl]-3(2H)-furanone

To a solution of 2-thiophenecarboxaldehyde (2.1 g, 19 mM) and 2,2,5-trimethyl-3(2H)-furanone (2.0 g, 15.9 mM) in ethanol (100 mL), was added 1N aqueous sodium hydroxide (1.6 mL, 1.6 mM). The reaction solution was stirred at room temperature for one day. After saturated aqueous sodium chloride (400 mL) was added, the aqueous layer was extracted with diethyl ether (3×100 mL). The combined ethereal extracts were washed with saturated aqueous sodium chloride (50 mL), dried over MgSO$_4$, filtered and concentrated to give a yellow solid. The product was recrystallized from hexane to afford a yellow crystalline solid (1.5 g, 43% yield), m.p. 75°–77° C.

Elemental analysis for $C_{12}H_{12}O_2S$: Calc'd: C, 65.43; H, 5.49. Found: C, 65.42; H, 5.45.

1% inhibition at 10 mg/kg.

EXAMPLE 24

5-[2-(Benzo[b]thien-2-yl)ethenyl]-2,2-dimethyl-3(2H)-furanone

To a solution of 2-benzothiophenecarboxaldehyde (1.5 g, 9.2 mM) and 2,2,5-trimethyl-3(2H)-furanone (1.6 g, 9.2 mm) in ethanol (100 mL), was added 1 N aqueous sodium hydroxide (1.2 mL, 1.2 mM). After the reaction solution was stirred at room temperature for one day, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a brown solid. The residue was purified by chromatography (silica gel, hexane-ethyl acetate) to afford a yellow solid (2.2 g, 58% yield), m.p. 103.5°–104° C.

Elemental analysis for $C_{16}H_{14}O_2S$: Calc'd: C, 71.08; H, 5.22. Found: C, 71.06; H, 5.21.

17% inhibition at 10 mg/kg.

EXAMPLE 25

5-[2-(3-Furanyl)ethenyl]-2,2-dimethyl-3(2H)-furanone

To a solution of 3-furaldehyde (1.26 g, 13.2 mM) and 2,2,5-trimethyl-3(2H)-furanone (1.5 g, 11.9 mM) in ethanol (50mL), was added 1N aqueous hydroxide (1.2 mL, 1.2 mM). After the reaction solution was stirred for one day at room temperature, saturated aqueous sodium chloride (400 mL) was added. The aqueous layer was extracted with diethyl ether (3×100 mL). The combined ethereal extracts were washed with saturated aqueous sodium chloride (50 mL), dried over MgSO$_4$, filtered and concentrated to give a yellow solid. The crude product was purified by chromatography (silica gel, hexane-ethyl acetate) to yield yellow crystals (1.8 g, 74% yield), m.p. 79°–80° C.

Elemental analysis for $C_{12}H_{12}O_3$: Calc'd: C, 70.57; H, 5.92. Found: C, 70.37; H, 5.60.

35% inhibition at 10 mg/kg.

EXAMPLE 26

2-Phenyl-2-methyl-5[2-(3-pyridinyl)ethenyl]-3(2H)-furanone

To a solution of 3-pyridinecarboxaldehyde (1.03 g, 9.6 mM) and 2,5-dimethyl-2-phenyl-3(2H)-furanone (1.0 g, 8 mM) in ethanol (50 mL), was added 1N aqueous sodium hydroxide (2.4 mL, 2.4 mM). The reaction solution was heated at 60° C. for 8 hours. After the reaction solution cooled to room temperature, saturated aqueous sodium chloride (200 mL) was added. The aqueous layer was extracted with diethyl ether (3×100 mL). The combined ethereal extracts were washed with saturated aqueous sodium chloride (50 mL), dried over MgSO$_4$, filtered and concentrated to give a brown solid. The crude product was purified by chromatography (silica gel, pet. ether-ethyl acetate) to afford a yellow crystalline solid (0.8 g, 36.3% yield), m.p. 106°–108° C.

Elemental analysis for $C_{18}H_{15}NO_2$: Calc'd: C, 77.96; H, 5.45; N, 5.05. Found: C, 77.70; H, 5.15; N, 4.97.

ED$_{50}$5 mg/kg.

EXAMPLE 27

2-Methyl-2-phenyl-5-[2-(4-pyridinyl)ethenyl]-3(2H)-furanone

To a solution of 4-pyridinecarboxaldehyde (1.4 mL, 14.9 mM) and 2,5-dimethyl-2-phenyl-3(2H)-furanone (2.0 g, 10.6 mm) in ethanol (50 mL), was added 1,8-diazabicyclo[5.4.0]undec-7-ene (DBU, 323 mg, 2.1 mM). The reaction solution was heated at 60° C. for 4 hours. After the reaction solution cooled to room temperature, saturated aqueous sodium chloride (400 mL) was added. The aqueous layer was extracted with diethyl ether (3×100 mL). The combined dichloromethane extracts were washed with saturated aqueous sodium chloride (50 mL), dried over MgSO$_4$, filtered and concentrated to give a red gummy product. The crude product was purified by chromatography (silica gel, pet. ether-ethyl acetate) to give a white crystalline solid (1.1 g, 37% yield), m.p. 165°–166° C.

Elemental analysis for $C_{18}H_{15}NO_2$: Calc'd: C, 77.96; H, 5.45; N, 5.05. Found: C, 77.73; H, 5.64; N, 5.05.

44% inhibition at 10 mg/kg.

EXAMPLE 28

2-Methyl-2-phenyl-5-[2-(2-pyridinyl)ethenyl]-3(2H)-furanone

To a solution of 2-pyridinecarboxaldehyde (1.2 mL, 1.2 mM) and 2,5-dimethyl-2-phenyl-3(2H)-furanone (1.5 g, 8 mM) in ethanol (15 mL), was added 1,8-diazabicyclo[4.5.0]undec-7ene (DBU, 0.2 mL, 1.3 mM). The reaction solution was heated at 80° C. for 5 hours. After the reaction solution cooled to room temperature, saturated aqueous sodium chloride (400 mL) was added. The aqueous layer was extracted with dichloromethane (3×100 mL). The combined dichloromethane extracts were washed with saturated aqueous sodium chloride (50 mL), dried over MgSO$_4$, filtered and concentrated to give a yellow solid. Purification by trituration with 10% diethyl ether in hexane gave a pale pink solid (887 mg, 40% yield), m.p. 74.5°–76° C.

Elemental analysis for $C_{18}H_{15}NO_2$: Calc'd: C, 77.96; H, 5.45; N, 5.05. Found: C, 77.66; H, 5.54; N, 5.11.

$ED_{50}$ 6 mg/kg.

EXAMPLE 29

4-[2-[2,3-Dihydro-2-phenyl-2-methyl-3-oxo-2-phenyl-5-furanyl]ethenyl]benzonitrile To a solution of p-cyanobenzaldehyde (0.84 g, 6.4 mM) and 2,5-dimethyl-2-phenyl-3(2H)-furanone (1.0 g, 5.3 mM) in ethanol (50 mL), was added 1N aqueous sodium hydroxide (0.5 mL, 0.5 mm). The reaction solution was stirred at room temperature for two days. Then, saturated aqueous sodium chloride (200 mL) was added. The aqueous layer was extracted with diethyl ether (3×100 mL). The combined ethereal extracts were washed with saturated aqueous sodium chloride (50 mL), dried over $MgSO_4$, filtered and concentrated to give a a beige solid. The crude product was recrystallized from ethanol to afford a yellow solid (671 mg, 42% yield), m.p. 187°–188° C.

Elemental analysis for $C_{20}H_{15}NO_2$: Calc'd: C, 79.72; H, 5.00; N, 4.65. Found: C, 79.64; H, 5.28; N, 4.71.

4% inhibition at 10 mg/kg.

EXAMPLE 30

2-Methyl-2-phenyl-5-[2-(3-thienyl)ethenyl]-3(2H)-furanone

To a solution of 3-thiophenecarboxaldehyde (1.07 g, 9.6 mM) and 2,5-dimethyl-2-phenyl-3(2H)-furanone (1.5 g, 8 mM) in ethanol (50 mL), was added 1N aqueous sodium hydroxide (1.6 mL, 1.6 mM). After the reaction solution was stirred at room temperature for one day, saturated aqueous sodium chloride (400 mL) was added. The aqueous layer was extracted with dichloromethane (3×100 mL). The combined dichloromethane extracts were washed with saturated aqueous sodium chloride (50 mL), dried over $MgSO_4$, filtered and concentrated to give a yellow liquid. The liquid was purified by chromatography (silica gel, pet. ether-ethyl acetate) to afford a yellow solid (1.6 g, 71% yield), m.p. 75°–77° C.

Elemental analysis for $C_{17}H_{14}O_2S$: Calc'd: C, 72.31; H, 5.00. Found: C, 72.29; H, 4.74.

EXAMPLE 31

4-[2-[2,3-Dihydro-2-(4-fluorophenyl)-2-methyl-3-oxo-5-furanyl]ethenyl]benzonitrile To a solution of p-cyanobenzaldehyde (1.6 g, 11.8 mM) and 2,5-dimethyl-2-(4-fluorphenyl)-3(2H)-furanone (2.0 g, 9.8 mM) in ethanol (75 mL), was added 1N aqueous sodium hydroxide (1.0 mL, 1 mM). After the reaction solution was stirred at room temperature for two days, saturated aqueous sodium chloride (400 mL) was added. The aqueous layer was extracted with dichloromethane (3×100 mL). The combined dichloromethane extracts were washed with saturated aqueous sodium chloride (50 mL), dried over $MgSO_4$, filtered and concentrated to give an orange liquid. The crude product was purified by chromatography (silica gel, pet. ether-ethyl acetate) to give a yellow crystalline solid (1.2 g, 38% yield), m.p. 140°–142° C.

Elemental analysis for $C_{20}H_{14}FNO_2$: Calc'd: C, 75.23; H, 4.42; N, 4.39. Found: C, 75.24; H, 4.31; N, 4.35.

1% inhibition at 10 mg/kg.

EXAMPLE 32

2-Methyl-2-(4-fluorophenyl)-5-[2-(2-pyridinyl)ethenyl]-3(2H)-furanone

To a solution of 2-pyridinecarboxaldehyde (1.26 g, 10.2 mM) and 2,5-dimethyl-2-(4-fluorophenyl)-3(2H)-furanone (2.0 g, 9.8 mM) in ethanol (100 mL), was added 1,8-diazabicyclo[5.4.0]undec-7-ene (DBU, 0.2 mL, 1.3 mM). The reaction solution was heated at 80° C. for 4 hours. After the reaction solution cooled to room temperature, saturated aqueous sodium chloride (400 mL) was added. The aqueous layer was extracted with diethyl ether (3×100 mL). The combined ethereal extracts were washed with saturated aqueous sodium chloride (50 mL), dried over $MgSO_4$, filtered and concentrated to give a yellow liquid. The crude product was purified by chromatography (silica gel, pet. ether-ethyl acetate) to yield a yellow solid (1.7 g, 59% yield), m.p. 70°–72° C.

Elemental analysis for $C_{18}H_{14}FNO_2$: Calc'd: C, 73.22; H, 4.78; N, 4.75. Found: C, 73.30; H, 4.61; N, 4.76.

92% inhibition at 10 mg/kg.

$ED_{50}$ 3.5 mg/kg.

EXAMPLE 33

2-(4-Fluorophenyl)-2-methyl-5-[2-(3-thienyl)ethenyl]-3(2H)-furanone

To a solution of 3-thiophenecarboxaldehyde (1.3 g, 1.2 mM) and 2,5-dimethyl-2-(4-fluorophenyl)-3(2H)-furanone (2.0 g, 9.8 mM) in ethanol (75 mL), was added 1N aqueous sodium hydroxide (2 mL, 2 mM). The reaction solution was stirred at room temperature for one day. After saturated aqueous sodium chloride (400 mL) was added, the aqueous layer was extracted with dichloromethane (3×100 mL). The combined dichloromethane extracts were washed with saturated aqueous sodium chloride (50 mL), dried over $MgSO_4$, filtered and concentrated to give a brown oil. The crude product was purified by chromatography (silica gel, pet. ether-ethyl acetate) to afford a yellow solid (1.8 g, 62% yield), m.p. 97°–98° C.

Elemental analysis for $C_{17}H_{13}SFO_2$: Calc'd: C, 67.98; H, 4.36. Found: C, 68.23; H, 4.47.

22% inhibition at 10 mg/kg.

The cytoprotective and anti-ulcer activities of the compounds of this invention were established by demonstrating their ability to prevent the formation of gastric mucosal lesions produced by ethanol following the procedure of Robert et al., Gastroenterology, 77 433 (1979), whereby male Sprague-Dawley rats weighing 120–150 g were fasted for 24 hours (ad libitum water). The rats were placed in individual cages and denied water 2 hours or more before testing. At a fixed time before administration of ethanol (usually 1 hour), the animals were orally administered either the test compound or its water-carboxymethylcellulose vehicle. Ethanol was then administered orally at a dose of 1 mL per animal. One hour after administration of the ethanol, the animals were sacrificed and their stomachs removed, cut along the greater curvature and flushed clean with tap water. Macroscopic lesions on the gastric mucosa were graded from 0–3 based upon the absence of lesions to the presence of lesions which approximate 6 millimeters in length. Comparison of the treated group with the control group permits expression of the results as percentage inhibition of lesion formation as a direct measure of cytoprotection. The $ED_{50}$ is calculated from a series of responses to different dosage levels of the compound being tested and serves to establish the dose at which half the animals did not develop lesions significantly different from the control group. The results of these studies are given at the end of each example illustrating the preparation of the tested compound, supra, as the percent inhibition or ED$_{50}$ where the latter value was determined.

Thus, the compounds of this invention may be administered neat or with a pharmaceutical carrier to a patient in need thereof. The pharmaceutical carrier may be solid or liquid.

A solid carrier can include one or more substances which may also act as flavoring agents, lubricants solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific gastric disorder must be subjectively determined by the attending physician. The variables involved include the specific disease state and the size, age and response pattern of the patient. Based upon the activity profile and potency of the compounds disclosed herein, an initial human dose within the range of about 1 to about 100 mg/day, by single or divided, oral administration, should be appropriate. The containing dose may then be modified to achieve the desired effect, within the range of about 0.5 to about 50 mg/day, as personalized for the patient.

What is claimed is:
1. A compound of the formula:

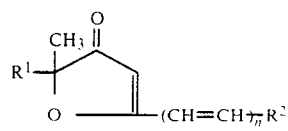

in which
R$^1$ is alkyl of 1 to 6 carbon atoms, phenyl or halophenyl;
R$^2$ is pyrazinyl; and
n is 1 or 2.
2. A compound of claim 1 in which R$^1$ is methyl, phenyl or 4-fluorophenyl, n is 1 and R$^2$ is pyrazinyl.
3. The compound of claim 1 which is 2,2-dimethyl-5-[2-(2-pyrazinyl)ethenyl]-3(2H)-furanone.
4. A pharmaceutical composition comprising a compound of the formula:

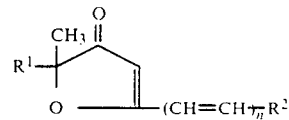

in which
R$^1$ is alkyl of 1 to 6 carbon atoms, phenyl or halophenyl;
R$^2$ is pyrazinyl; and
n is 1 or 2;
and a pharmaceutical acceptable carrier therefor.
5. A pharmaceutical composition of claim 4 in which R$^1$ is methyl, phenyl or 4-fluorophenyl, n is 1 and R$^2$ is pyrazinyl; and a pharmaceutical acceptable carrier therefor.
6. A method for preventing gastric ulcers which comprises administering, orally or parenterally, to a mammal in need thereof a cytoprotective amount of a compound of the formula:

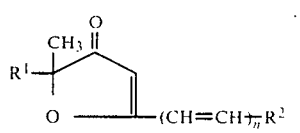

in which
R$^1$ is alkyl of 1 to 6 carbon atoms, phenyl or halophenyl;
R$^2$ is pyrazinyl; and
n is 1 or 2.
7. A method for treating gastric ulcers which comprises administering, orally or parenterally, to a mammal suffering from gastric ulcers an anti-ulcer amount of a compound of the formula:
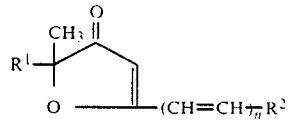
in which
 R[1] is alkyl of 1 to 6 carbon atoms, phenyl or halophenyl;
 R[2] is pyrazinyl; and
 n is 1 or 2.
* * * * *